United States Patent [19]

Higashi et al.

[11] Patent Number: 4,682,503
[45] Date of Patent: Jul. 28, 1987

[54] MICROSCOPIC SIZE, THERMAL CONDUCTIVITY TYPE, AIR OR GAS ABSOLUTE PRESSURE SENSOR

[75] Inventors: Robert E. Higashi, Bloomington; Steven D. James, Edina; Robert G. Johnson, Minnetonka; Ernest A. Satren, Bloomington, all of Minn.

[73] Assignee: Honeywell Inc., Minneapolis, Minn.

[21] Appl. No.: 863,892

[22] Filed: May 16, 1986

[51] Int. Cl.[4] .......................................... G01L 21/12
[52] U.S. Cl. ...................................... 73/755; 73/204; 338/318; 357/55
[58] Field of Search ................... 73/755, 204; 357/55; 338/318, 319

[56] References Cited

U.S. PATENT DOCUMENTS

| | | | |
|---|---|---|---|
| 3,359,462 | 12/1967 | Schutze et al. | 317/101 |
| 4,343,768 | 8/1982 | Kimura | 73/204 |
| 4,389,429 | 6/1983 | Soclof | 29/580 |
| 4,472,239 | 9/1984 | Johnson et al. | 357/55 |
| 4,478,076 | 10/1984 | Bohrer | 73/204 |
| 4,478,077 | 10/1984 | Bohrer et al. | 338/318 |
| 4,542,650 | 9/1985 | Renken et al. | 73/204 |
| 4,548,078 | 10/1985 | Bohrer et al. | 73/204 |
| 4,549,433 | 10/1985 | Gneiss et al. | 338/318 |
| 4,624,137 | 11/1986 | Johnson et al. | 338/319 |

Primary Examiner—Donald O. Woodiel
Attorney, Agent, or Firm—Omund R. Dahle

[57] ABSTRACT

A microscopic size absolute pressure sensor for air or gas of the thermal conductivity type, a silicon nitride covered silicon microchip has an elongated V-groove anisotropically etched in the silicon with a heated silicon nitride bridge element extending over the surface of the V-groove.

20 Claims, 29 Drawing Figures

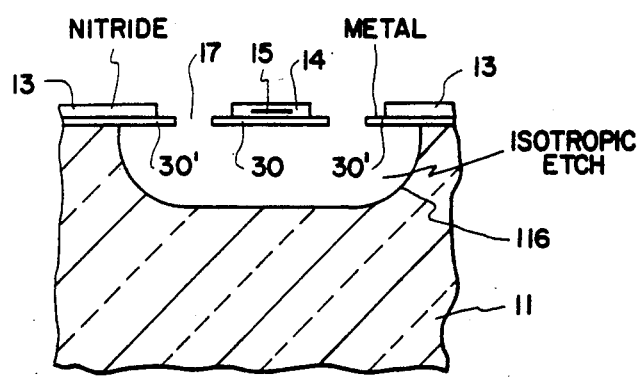
Fig. 12
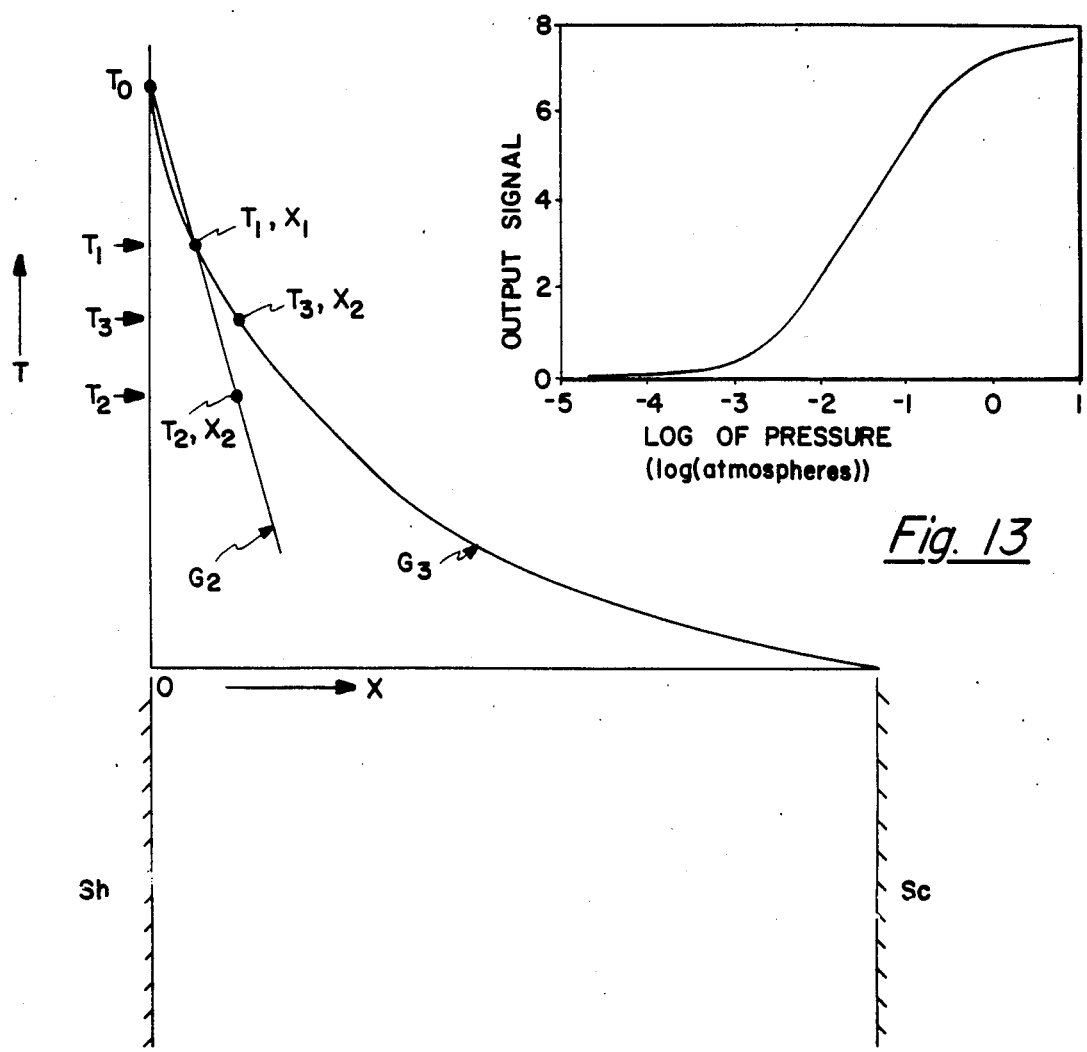
Fig. 13
Fig. 1b

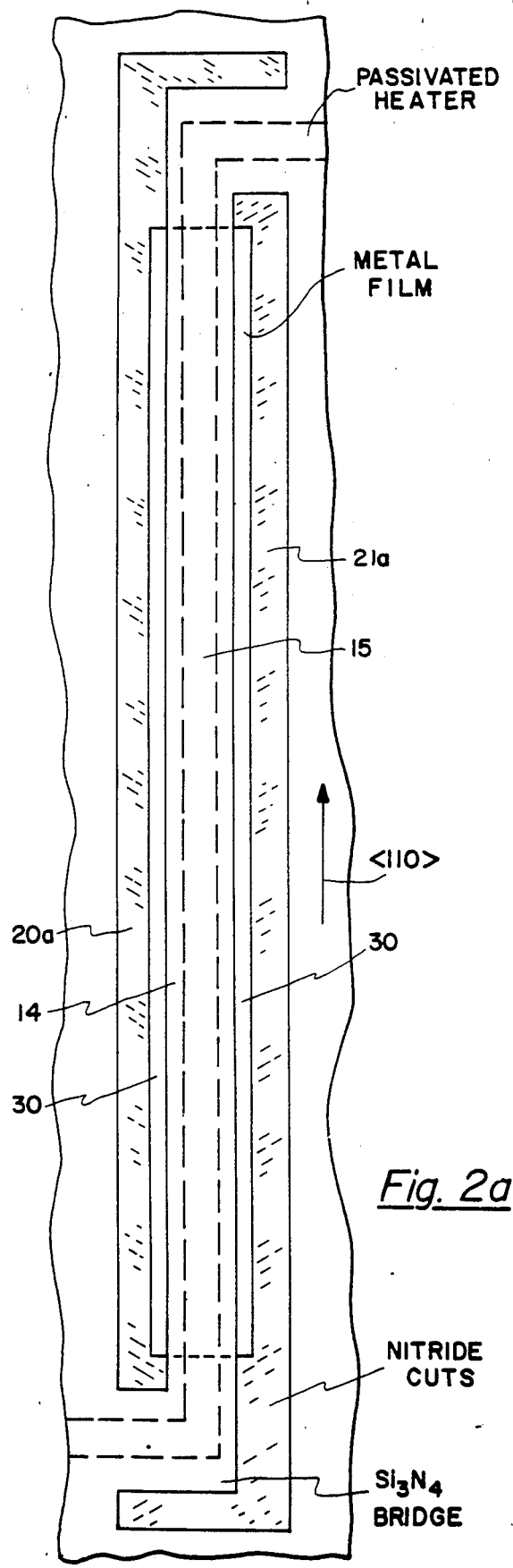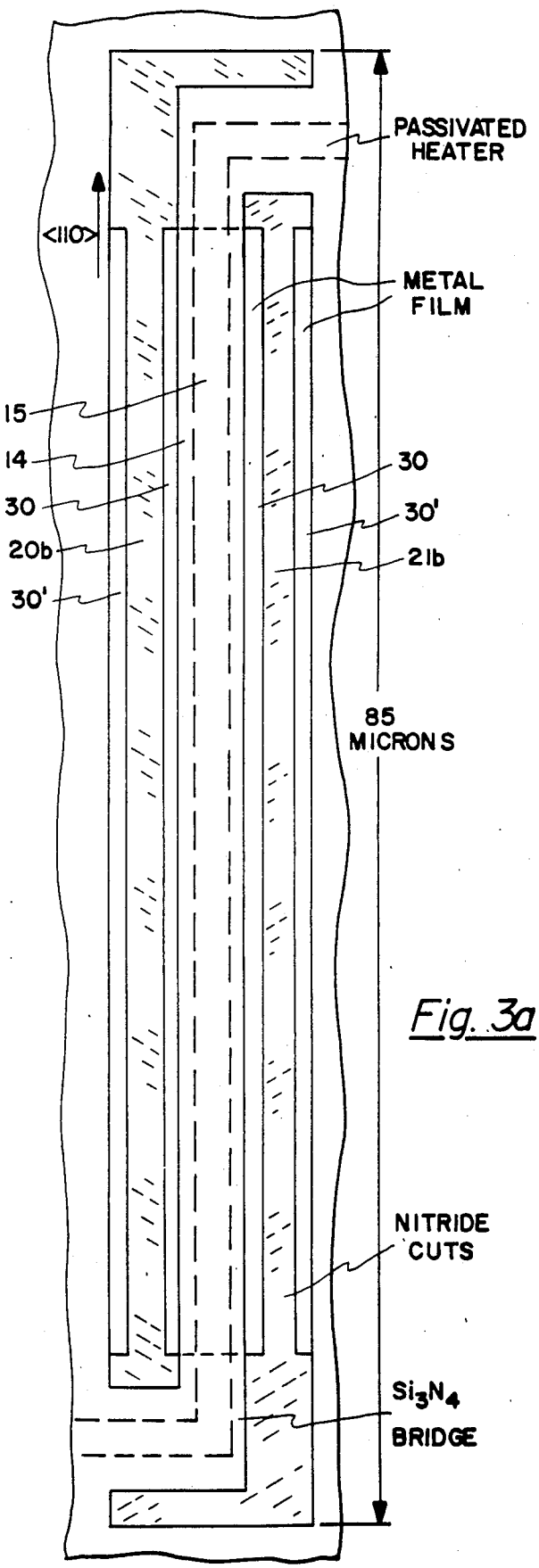
Fig. 2a
Fig. 3a

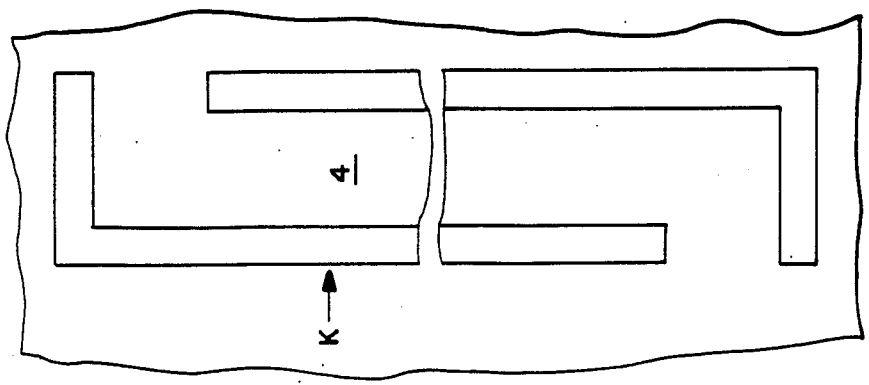
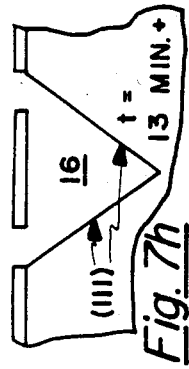
Fig. 7g
Fig. 7h
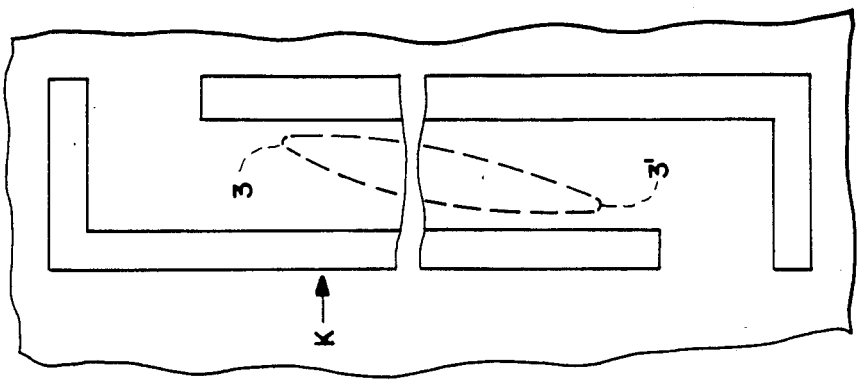
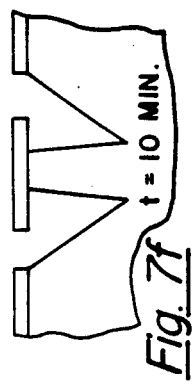
Fig. 7e
Fig. 7f
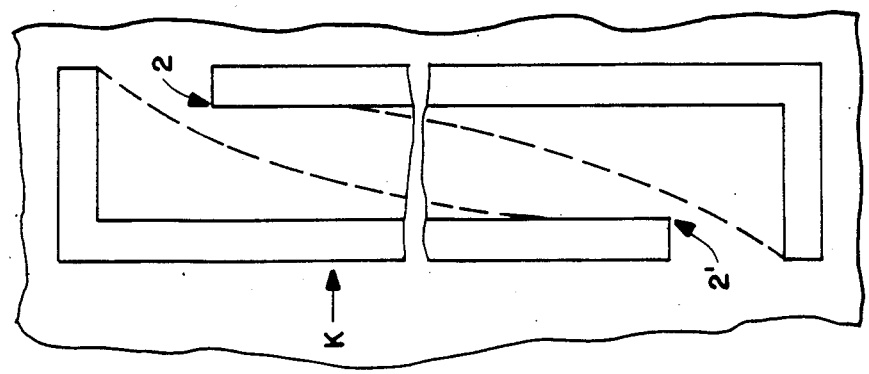
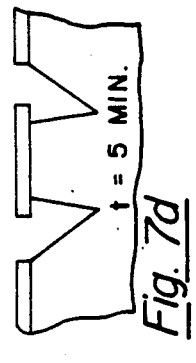
Fig. 7c
Fig. 7d
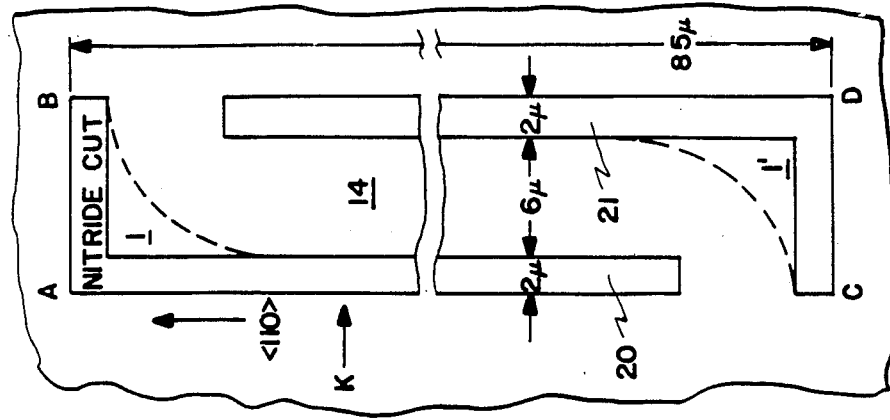
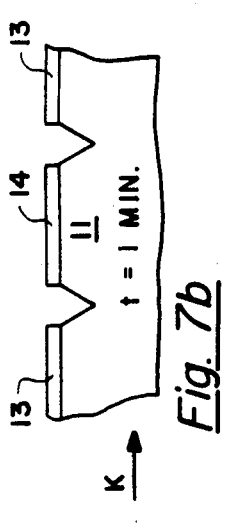
Fig. 7a
Fig. 7b

MICROSCOPIC SIZE, THERMAL CONDUCTIVITY TYPE, AIR OR GAS ABSOLUTE PRESSURE SENSOR

BACKGROUND OF THE INVENTION

The thermally conductive response of the sensor of the present invention to pressure change is believed to depend substantially on the corresponding change of gas density in the vicinity of the thin edge of a hot silicon nitride film where a strong, non-linear temperature gradient exists. It is well known that there is no thermally conductive response to pressure change if the thermal gradient is linear, that is, if the temperature profile has a constant or nearly constant slope and if the molecular mean free path is relatively small. It was not well known, nor was it obvious prior to our experimental realization of the effect in thin films, that the non-linear thermal gradient could play a significant role in pressure sensing. We will now explain the reason for the effect of the non-linear thermal gradient on the pressure response.

FIG. 1b depicts on the left a hot surface, $S_h$ at a temperature $T_o$, and on the right a cold surface, $S_c$. All molecules striking the hot surface are assumed to equilibrate with temperature $T_o$ before rebounding. Shown also is a linear temperature profile, $G_2$, as for planar surfaces, compared with a non-linear profile, $G_3$ associated with a sharply curved hot surface.

Consider first the linear gradient, and take the molecular mean free path to be a length of $X_1$. Molecules leaving point $X_1$ will arrive at the surface with an average temperature of $T_1$ and will cool the surface in proportion to the difference $T_o-T_1$. If the pressure is reduced by a factor of two, the mean free path doubles to a length $X_2$, and molecules that formerly struck the surface from point $X_1$ now strike it from point $X_2$, and have a temperature, $T_2$, such that $T_o-T_2=2(T_o-T_1)$. Now each molecule reaching the surface has twice the cooling capability, but exact compensation occurs because the molecular density is reduced by a factor of two. Consequently the rate of heat transport is unchanged, and will remain so until the mean free path length approaches the spacing between the two surfaces. Beyond this critical length, the above described compensation fails and the thermal conductance of the gas decreases with decreasing pressure until the density of the gas is so low that no appreciable cooling occurs.

Next consider the curved temperature profile, $G_3$, having the non-linear gradient as shown. In this case, reducing the pressure by a factor of two and thus doubling the mean free path to a length equal to $X_2$ does not compensate. It does not proportionally increase the temperature differential because, clearly, $(T_o-T_3)<2(T_o-T_1)$. Therefore the cooling capability of the molecules reaching the hot surface is less in the case of the non-linear gradient as the pressure is reduced, even when the mean free path is very short compared to the spacing between the surfaces. In effect, the thermal gradient near the surface is reduced as the pressure is reduced.

The magnitude of the pressure effect is proportional to the non-linearity that is achieved by shaping the hot surface into a sharp point or edge. However the magnitude of the total effect in all the gas surrounding the hot surface depends on the sum of all conductance paths, the more linear paths diluting the effect of the strongest non-linear regions. Ideally, all the thermal conductance of the gas around the heated bridge microstructure should occur in the strongly non-linear region. Conductance elsewhere in the more linear gradient regions is little changed by gas density variation, and therefore dilutes the corresponding total conductance variation. It is desirable to maximize the non-linear proportion of the total conduction, but before discussing this it is informative to compare the operation of the present invention with the well known Pirani and thermocouple vacuum gauges of the prior art.

The thermocouple and Pirani gauges also use a thermal conductance principle for measuring pressure. They operate typically in the 1-1000 micron (about $10^{-6}$ to $10^{-3}$ atmosphere) range. In these devices the useful operation begins when the gas density falls to the point at which the mean free path of the gas molecules increases to a critical length comparable to the heated wire diameter, and which is analogous to the critical length between planar surfaces. Useful operation ends when the gas density falls further to the point at which the mean free path is substantially larger than the gauge housing. The major effect contributing to the response is the reduction in the density of molecules below the critical density required to compensate and to maintain constant thermal conductance. This occurs when the mean free path length of the molecules exceeds the diameter of the heater wire. A minor effect also contributing to the response is the effect of the non-linear gradient near the heated wire surface. The thermal gradient around a wire varies as $1/r$, where r is the distance from the center of the wire. Because the wire is suspended openly without any nearby heat sink, however, the non-linear gradient is small near the wire surface, and its effect on the total conductance is diluted by the long, much more linear remainder of the conductance path to the housing wall over most of which r is large and the gradient is more linear. For example, the wire radius might be 0.002", and the distance from the wire to the housing wall might be 0.500", with the most effective non-linear region within a few thousandths of an inch of the wire. Thus, the effect of the non-linear gradient on the total responses of the piror art gauges is of limited significance.

The sensor of the present invention is distinguished from the above discussed prior art gauges in that it is responsive to pressure change over a range from about $10^{-4}$ atmosphere to 10 atmospheres pressure in contrast to the prior art gauges whose range is within $10^{-6}$ to $10^{-3}$ atmosphere. The present invention is also distinguished from the prior art gauges in that the principal contribution to its pressure response over all but the lowest part of the pressure range is due to an enhanced, non-linear gradient effect. Only when the molecular mean free path becomes one micron or longer below 0.1 atmosphere near the lowest part of its pressure range does the critical length of the molecular mean free path significantly affect the response.

This greatly expanded operating pressure range is due in part to the approximately 100 times smaller thickness of the heated microstructure bridge compared to the prior art wire diameter. Thus our invention provides a much stronger and more non-linear thermal gradient. An equally significant factor is the presence of a nearby heat sink. We have found that the non-linear gradient is further strengthened and the operating pressure range is increased by placing the edge of the heated microstructure bridge very close to a cold heat sink, for example, within a 1-3 micron distance. This configuration enables the conductance through the strong, non-linear region to be a large fraction of the total conductance of the paths near the edge. Because the close edge spacing makes the gradient very large there, a substantial part of the total thermal conduction from the heated microstructure bridge occurs in the edge region, and therefore a substantial fraction of the total conduction also occurs through the strongest non-linear region. Consequently, the change of total conductance corresponding to a pressure change is quite large, and the large magnitude of the non-linear gradient makes the sensor responsive to pressures up to at least ten atmospheres which is about ten thousand times higher than the upper end of the pressure range of the prior art Pirani and thermocouple gauges.

Although the entire heat flow from the heated microstructure bridge should be through the strong non-linear thermal gradient region, in practice it is difficult to design and fabricate a microstructure bridge in which this objective is attained. The ideal geometry would be a microstructure wire of circular cross section within a hollow cylinder heat sink, with the wire radius and spacing from the sink in the micron range, and optimumly selected for the desired pressure range.

We know of no practical method for the fabrication of such a wire and cylinder microstructure. However, microstructure techniques that we have developed do enable the fabrication of heated films of rectangular cross section having thicknesses of less than one micron, and having the film edges spaced one micron or less, or a few microns from a colder heat sink consisting of a silicon edge or corner, or a cold metal film edge, or a cold nitride film edge, or a combination of these. Dielectrics other than nitride could also be used. Thus the non-linear effect can be achieved in the desired range of dimensions, but with a part of the total heat flow also occurring through regions away from the edge where the gradient is more linear.

To maximize the non-linear effect, the edges of the microstructure bridge should be close to the cold heat sink with minimal heat flow through the broad areas of smaller gradients away from the edges. Thus the width of the microstructure bridge should be as small as possible consistent with fabrication tolerances of the design in which the heater film is preferably, but not necessarily, passivated by enclosure within silicon nitride or some other dielectric. Three designs embodying these principles are shown in FIGS. 1, 2 and 3, and will be described in detail.

SUMMARY OF THE INVENTION

The present invention falls in the catagory of a microscopically small, thermal conductivity type of air or gas absolute pressure sensor, fabricated on a silicon chip, and which is designed to have a strongly non-linear temperature gradient, and to have as much of the conductance as possible in the non-linear region. Since the detector is microscopically small, detectors for many ranges can be fabricated on the same silicon chip whereby a single silicon chip can be used to cover a broad range of combined pressures. Compared to the microscopically small absolute pressure sensor of the present invention, the diaphragm pressure sensors of the prior art are bulky and commonly require overload protection against rupture. The present invention also does not require an evacuated reference volume. In other prior art, the Pirani and thermocouple vacuum gauges are much larger and have responses that depend primarily on thermal conductance changes caused by molecular mean free paths of length comparable to or greater than a heated wire diameter, whereas in the present invention the response is principally due to relatively smaller mean free paths interacting with strong non-linear thermal gradients near sharp heated edges.

BRIEF DESCRIPTION OF THE DRAWINGS

FIGS. 1a, 1b, 2a and 3a are top plan views of the sensor of FIGS. 1, 2 and 3, respectively while FIG. 1b is a graphical representation.

FIGS. 7a, b, c, d, e, f, g and h show anisotropic etch progression in etching the V-groove under the silicon nitride bridge.

FIGS. 10, 10a, 11, 11a and 12 are modifications of FIGS. 3 and 3a.

FIG. 13 is a graphical representation of responsivity to air pressure.

DESCRIPTION

Figure 1:
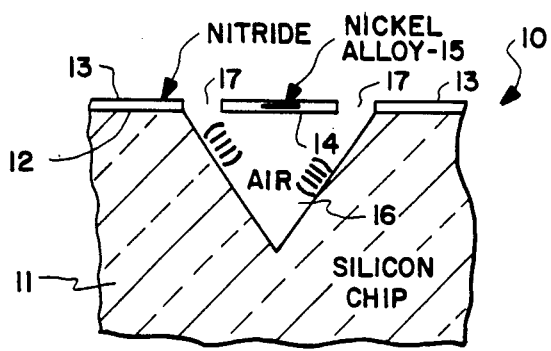
FIGS. 1, 2 and 3 are cross-sectional views of several embodiments of our absolute pressure sensor.

The objective in developing a thermal conductivity type of absolute pressure sensor is to achieve a strongly non-linear temperature gradient, and to have as much of the conductance as possible in the non-linear region. We teach in our thermal conductance measurement device an electrically heated element, heated by current conduction to an elevated temperature substantially above that of an adjacent heat sink. Our device has a silicon substrate heat sink with a narrow V-groove or depression having bare silicon surfaces. It has a suspended sensor member means consisting of a resistance metal film laminated in thin film silicon nitride in the form of a bridge over the V-groove supported by the silicon only near the ends of the bridge. Dielectric materials other than silicon nitride could also be used, such as for example, $SiO_2$. Other groove shapes could also be used such as, for example, a truncated V-groove having a flat bottom of etch resistant boron doped silicon formed initially beneath a layer of epitaxially grown silicon as is common in the art, and such as in another example, a groove made by an isotropic etch. The simple V-groove formed by a conventional anisotropic etch of KOH and water is preferred because it is a simple method and because it results in a precisely controlled size and shape of the groove beneath the sensor member means due to the etch resistant (111) bounding planes that form the sides and ends of the groove.

The air or gas pressure sensor disclosed herein uses the effect of a decrease of thermal conductance of the gas near the detector with decreasing density when the mean free path between molecular collisions begins to be an appreciable fraction of the distance across a temperature gradient change in the gas.

We have found by experiment that our pressure sensor device depends for its maximum response and best practical operation on the close proximity of a hot, sharp edge to a cold heat sink. The elongated dielectric bridge encasing the conductive heater provides the hot, sharp edge running closely parallel to the cold substrate heat sink V-groove. Silicon has a metal-like thermal conductance of 1.2 w/cm°C. and so is an excellent heat sink. The proximity of the silicon nitride bridge edge to the heat sink is preferably 2 microns or less.

We achieve this hot-edge effect by enclosing an elongated very thin metal film heater of high resistivity within a silicon nitride passivating film, suspending this elongated silicon nitride bridge over a V-groove in (100) silicon substrate and attaching the bridge to the silicon near the ends of the V-groove. The anisotropically etched V-groove preferably has a length about 8 times its width and the silicon nitride bridge preferably has a length/width ratio of about 10–15. In one successful embodiment, the length of the V-groove is about 85 microns and the width about 10 microns; the thickness of the silicon nitride film is 0.6–0.8 micron and the width of the bridge about 6 microns. In this type structure most of the heat is conducted away from the thin film heater laterally through the width of the silicon nitride bridge, and then through the intervening 2 micron air or gas path to the adjacent closely-spaced silicon surface.

Although the silicon nitride is less thermally conductive than the NiFe thin film heater (the ratio of conductivities is 0.195/0.25, i.e. 1/12.8), the silicon nitride is 81 times more thermally conductive than air (the ratio of conductivities is 0.0195/0.00024). Consequently there is very little temperature drop across the two micron width of the silicon nitride from the heater to the edge, compared to the temperature drop across the two micron air gap to the silicon. Therefore the silicon nitride, to a good approximation, is an isothermal surface very close in temperature to the enclosed heater film.

We achieve a sharp edge that is heated with the thin film technology. Because we require adequate strength in the elongated bridge and because of fabrication tolerances, this bridge structure is typically 6 microns in width by 0.6 microns thick or less, with a typical bridge cross section width to thickness ratio of about 10 to 1. This ratio is not limiting, however, because ratios much larger and much smaller also give quite useful responses.

The action of the pressure sensor is believed to depend on the highly non-linear temperature gradient at the thin edge of the silicon nitride thin film. Therefore we try to maximize the thermal conduction through the non-linear gradient near the edge and to minimize it elsewhere. That is, we try to minimize thermal conduction through the air path from the central region of the bridge cross section to the lower parts of the surface of the silicon groove. In this respect, the longer conduction path provided by a V-groove is superior to a flat bottomed, truncated groove of the same width.

To be described is a semiconductor chip mounted pressure sensor of small dimensions, typically less than 100 microns in length comprising a thin, sharp-edged self-heated dielectric member means and resistive bridge of large length to width ratio, and wherein the edges of the dielectric bridge are placed close to an adjacent heat sink of high thermal conductivity. The spacing between the center area (in cross section) of the bridge member and the heat sink surface is much greater than the edge spacing. The dielectric bridge is heated by its enclosed electrically resistive thin film.

Referring now to FIG. 1 there is generally disclosed in cross section a microbridge pressure sensor 10 comprising a semiconductor substrate 11, such as a single crystal silicon chip. The silicon substrate 11 is a heat sink for the sensor and supports the other elements of the sensor. The silicon substrate surface 12 has formed thereon a thin film layer 13 of a dielectric, such as silicon nitride. This thin film layer may be about 0.6–0.8 micron in thickness. Embedded in a bridge portion 14 of the silicon nitride layer is a thin film resistive heater 15, which may be a nickel alloy such as a NiFe type commonly known as Permalloy. Additional nitride covers the heater 15 so that it is passivated. This silicon nitride is then masked and etched or ion milled to expose narrow channels (nitride cuts) to the silicon surface. Complete passivation is desirable but not necessary in all applications. For example, the heater 15 could extend to the edges of the nitride cut in FIG. 1, or, alternatively, the cut could be ion milled through the nitride and the heater film to form a bridge portion 14 only 2 microns wide having the nickel-iron alloy 15 exposed at its edges. From these nitride cuts an etched cavity or V-groove 16 in the silicon is fabricated by anisotropic etching as described in more detail below. The cavity may be, for example, about 7 microns deep and about 10 microns wide at the surface. We have made larger, deeper cavities, however. An air gap 17 of about 2 microns separates the bridge edge from the V-groove.

Figure 1A:
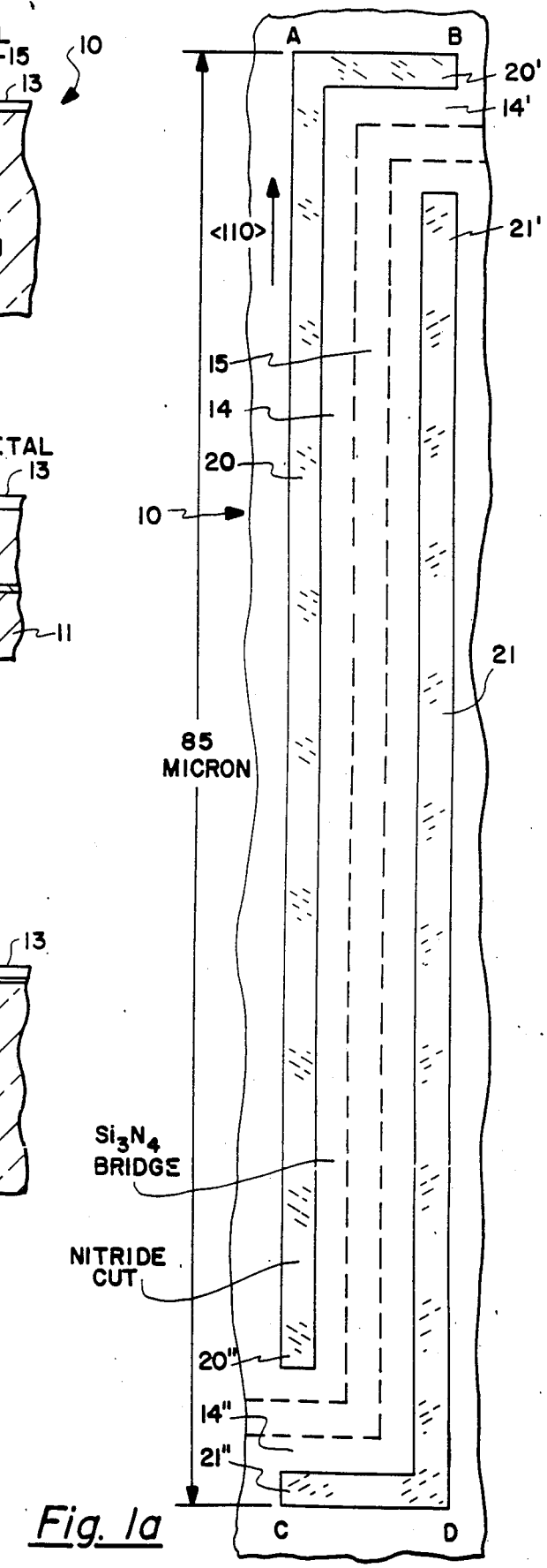

FIG. 1a is a top plan view of the pressure sensor 10 of FIG. 1. The structure consists of a narrow microbridge suspended over a long narrow micro cavity etched anisotropically. The cavity is oriented with its long axis in the <110> (or equivalent) silicon crystal direction in the surface of a (100) silicon wafer. Element 14 is the thin film silicon nitride bridge within which the two micron wide NiFe resistor 15 is formed. The required opposing L-shaped cross-hatch areas 20 and 21 are the preliminary etch cuts through the silicon nitride 13 to the silicon surface 12. This etch through the silicon nitride is preferably made by a conventional plasma etch process or by ion milling. The successive anisotropic etch for the silicon is applied through the nitride cuts 20 and 21 to form in the silicon the narrow V-shaped cavity 16 with corners at A, B, C, D and having the cross section as shown in FIG. 1. This anisotropic etchant is preferably a conventional potassium hydroxide anisotropic etch. The cavity 16 preferably is less than 100 microns long. The (111) sides provide a natural etch stop. It will be apparent that with the two opposing and interlocking L-shaped cuts 20 and 21 through the silicon nitride, the bridge abutments or termini 14' and 14" must be different, with the abutments joining the bridge 14 to the chip 10 between the end of long element or leg 21' of cut 21 and short element or leg 20' of cut 20 for abutment 14', and between the end of long element or leg 20" of cut 20 and short element or leg 21" of cut 21 for abutment 14". The abutments 14' and 14" are at diagonally opposite segments of the long edges rather than directly at the ends of the bridging element 14. The air gaps 17 of FIG. 1 result from the nitride cuts 20 and 21 of FIG. 1a. FIG. 1a shows the elongated sensor-heater 15 entering the bridging element 14 at abutment 14' passing down the center of the bridge and leaving at abutment 14". If higher resistance values are desired, than occurs in a single bridge, additional structures can be connected in series.

Figure 2:
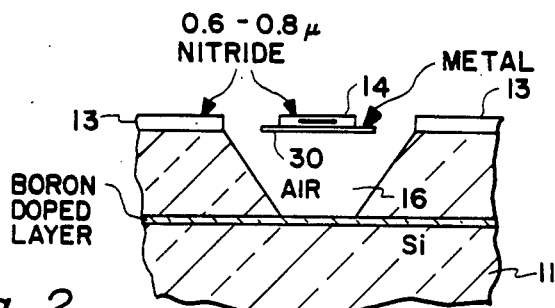

In FIG. 2 there is shown another embodiment of our invention. In this modification, a metal film or layer of metal 30 is attached to the bottom of the silicon nitride bridge 14 with the metal edges extending beyond the nitride edge by 2 or 3 microns. The metal could be NiFe with thermal conductivity about 10 times that of silicon nitirde, or chrome with thermal conductivity about 45 times that of silicon nitride. The metal thickness can therefore be 10 times or 45 times less respectively than the silicon nitride layer with no loss of conductance from heater to edge. Consequently, metal films in the neighborhood of 0.1 micron can be used to greatly increase the non-linearity of the thermal gradient at the edge, and thus to provide a larger and more linear response over higher pressure ranges.

The non-linear gradient region is primarily associated with the edge of the microbridge, and the thinner (i.e., the sharper) the edge, the stronger is the non-linear field, and the larger will be the output signal, particularly at high pressures in the 1 to 10 atmosphere range. The thinness of the silicon nitride layer and its edge is limited by the requirement that the microbridge be supported in a rigid manner, and that the thermal impedance remains low between heater and edge. The lower limit for the silicon nitride thickness is therefore in the neighborhood of 0.4 micron. In FIG. 2 this limitation is avoided. A normal silicon nitride thickness of 0.6–0.8 micron is retained plus the addition of a metal layer 30 fastened to the bottom of the bridge with the metal edges extending beyond the nitride edge.

Referring now to FIG. 2a, there is shown a top plan view of the embodiment of FIG. 2. It is similar in many respects to FIG. 1a. The main differences are in the adjustments to the shape of the nitride cuts 20a and 21a to accomodate the metal edges 30 extending beyond the silicon nitride.

Figure 3:
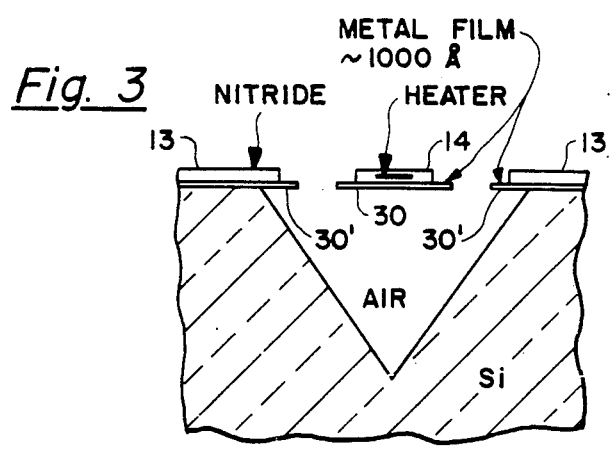

Another modification is shown in FIG. 3 in which the metal underlies the silicon nitride at the edges 30' of the V-groove as well as at the bridge. In this embodiment the two opposed metal edges are used effectively because of the high conductance of the metal. FIG. 3a is the top plan view of the embodiment of FIG. 3. The nitride cuts 20b and 21b are modified from those of FIGS. 1a and 2a.

The several embodiments are all heated by a current flowing through resistive path 15. The operation of the sensor is based on measuring the resistance required to maintain the heater element at a given temperature. When an increase in pressure occurs, there comes an increase in molecular density of the gas surrounding the bridge 14. Increasing molecular density increases the thermal conduction in the non-linear gradient region, correspondingly accelerating the transfer of heat from the sensor. This increase in molecular density thus causing an accelerated heat dissipation, and tends to cause a lower temperature of the bridge 14, and therefore a lower resistance, thus requiring a higher voltage and current to maintain the temperature of the resistor 15. The loss of heat translates into a power change which allows a determination of the absolute pressure.

Figure 4:
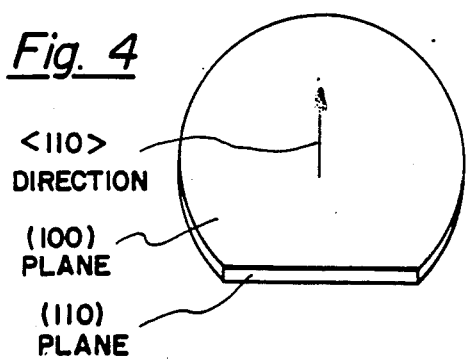
FIG. 4 is a pictorial representation of crystal orientation in the silicon wafer used in the fabrication of the present sensor.

FIG. 4 is a pictorial representation of crystal orientation used in the fabrication of the present absolute pressure sensor. There is shown a conventional silicon wafer with the top surface in the (100) plane, the flat edge in the (110) plane and the <110> direction of the crystal. In the fabrication of this microscopic size sensor configuration it is significant that the edge of the silicon nitride bridge and the nitride cut is in the <110> direction as shown in FIGS. 1a, 2a and 3a. With this orientation of the bridge and nitride cuts relative to the silicon direction, the stage is prepared so that the anisotropic etching of the silicon proceeds without widening the necessary narrow gap between the sharp edge of the silicon nitride bridge and the wall of the V-groove. This sharp edge relation shown in FIGS. 1, 2 and 3 is significant in having a non-linear thermal gradient across the air gap.

Figure 5A:
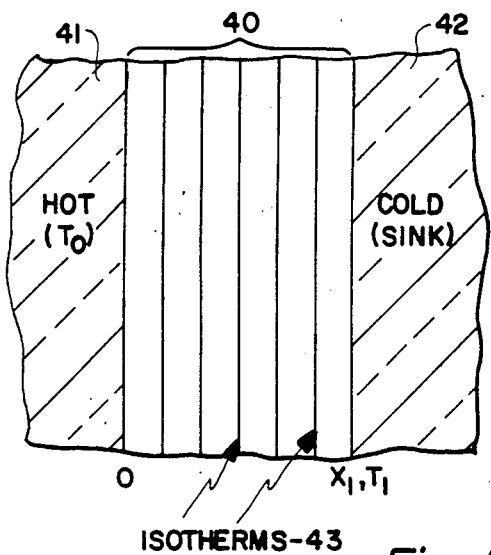
FIGS. 5a, b, c and d are pictorial and graphical representations of linear vs. non-linear thermal gradients across an air gap.
Figure 5B:
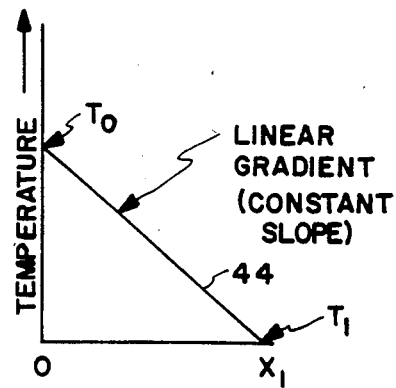
Figure 5C:
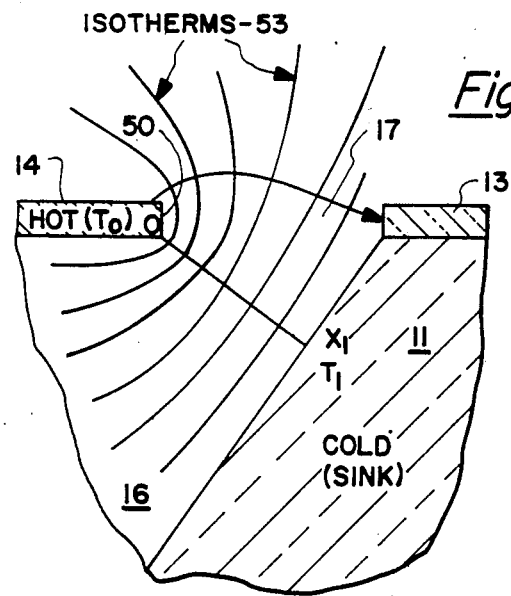
Figure 5D:
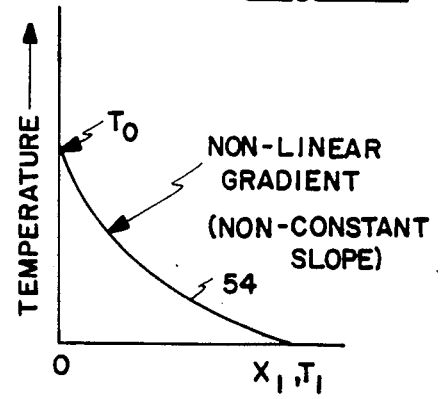

Referring now to FIGS. 5a and b versus FIGS. 5c and d there is compared a linear thermal gradient versus a non-linear thermal gradient. In thermal fields in which the thermal gradient is constant, or changing very slowly, thermal conductance is not appreciably dependent on gas pressure (density). When the gradient non-linearity is very strong, thermal conductance increases with increasing density, or pressure (assuming constant temperature of the gas). FIGS. 5a and b which has a linear thermal gradient across the air gap 40 from the hot surface 41 to the cold sink 42 will not be usable as a pressure sensor in which the mean free molecular path is small compared to the spacing 40. The isotherms 43 are equally spaced resulting in a straight line constant slope plot 44 of temperature versus distance x, shown in FIG. 5b. In contrast, the structure of FIG. 5c, which is an enlargement of a portion of FIG. 1, shows that the sharp edge 50 of the hot silicon nitride bridge 14 has a non-linear thermal gradient to the silicon heat sink. The non-linear isotherms 53 are plotted in FIG. 5d to show the non-linear gradient curve 54 of temperature as a function of distance across the air gap 17.

Figure 6:
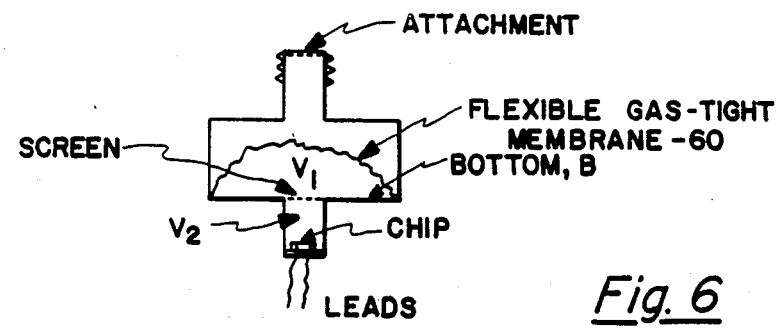
FIG. 6 is a diagrammatic representation of the sensor mounted in a sealed chamber to control the gas constituents in the sensor environment.

FIG. 6 shows an exemplary mounting arrangement for the chip containing the pressure sensor 10 beneath a flexible gas-tight membrane 60 which keeps the sensor in a known gas composition. It also protects the chip from contaminants. The design specifies: (1) that the membrane not be in tension in the specified pressure range, (2) that the volume, $V_1$, be much larger than $V_2$ so that the specified pressure range can be broad, and such that at the low end of the pressure range the membrane is fully extended but without appreciable tension, and at the high end, the membrane is crumpled on the bottom surface, B. The pressure range then is the ratio of $(V_1+V_2)/V_2$ which can conveniently be made quite large without adding diaphragm tension effects to the detector response.

The anisotropic etching of the microscopic pit or V-groove in the silicon is further illustrated in FIGS. 7a–h, where the general progression of the anisotropic etch is observed. In FIG. 7a is shown that the long axis of the bridge 14 lies in the <110> silicon crystal direction. This orientation, or the equivalent orientation <101> or <011> is essential in order to anisotropically etch a V-groove or pit which has as its outside dimensions A,B,C,D. In order to be able to anisotropically etch the silicon, there must first be nitride cuts 20 and 21 made through the silicon nitride layer 13. As is shown in FIG. 7a these cuts are about 2 microns in width and leave a silicon nitride bridging material inbetween about 6 microns wide. In order to accomplish the etch of the rectangular pit, as shown, the two nitride cuts are made L-shaped. The short leg AB of nitride cut 20 is about 10 microns long as is short leg CD of cut 21.

The anisotropic silicon etch first etches small V-grooves in the silicon as shown in FIG. 7b as the etch starts to undercut only on the outside corners 1 and 1'.

The heavy dashed line (FIG. 7a) is the advancing edge of the undercut as seen through the silicon nitride. When in FIG. 7c the undercut breaks through into the neighbor V-groove at point 2 and 2', a sharp corner forms at 2,2' which is rapidly eaten away towards 3,3' as shown in FIG. 7e. The last little pillar of silicon disappears soon after at 4 (FIG. 7g) leaving a V-groove pit 16 (FIG. 7h) bounded by (111) silicon planes. The etch progression time (shown in minutes) in FIGS. 7b, d, f and h are approximate or representative.

Figure 8:
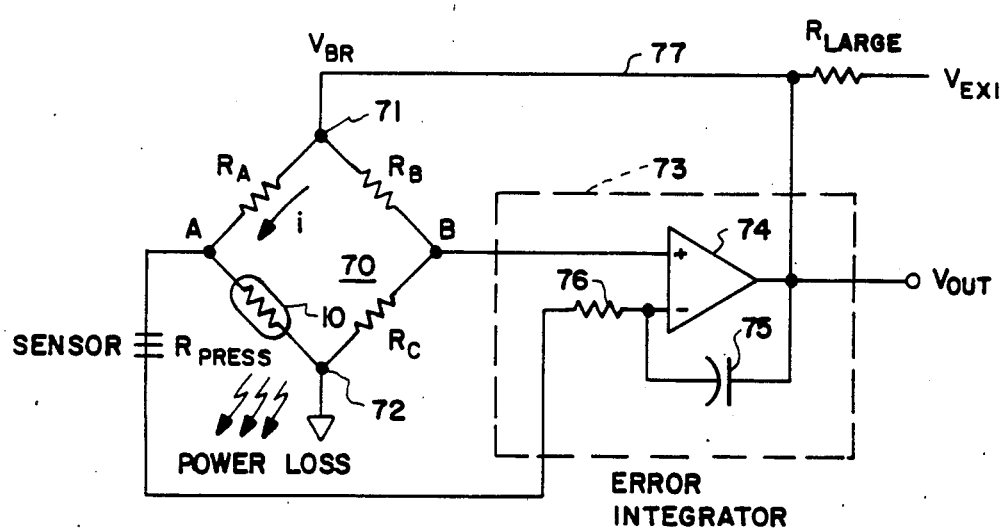
FIG. 8 is a schematic diagram of a typical circuit arrangement in which the sensor of this invention operates.

Referring now to FIG. 8 there is shown a representative circuit in which the absolute pressure sensor 10 is used. An electrical bridge 70 has power input points 71 and 72 and output terminals A and B. Resistors $R_A$, $R_B$, $R_C$ and sensor 10 are connected to complete the bridge. $R_A$, $R_B$ and $R_C$ are external discrete resistors. An error integrator 73 comprising an amplifier 74, capacitor 75 and resistor 76, is connected to receive the output signal from terminals A and B of bridge 70. A conductor 77 connects the error integrator output back to input terminal 71 of the bridge.

DETAILED DISCUSSION OF CIRCUIT OPERATION

The Wheatstone bridge will be balanced when voltage of points A and B are the same. This is essentially two voltage dividers with $$V_A = V_{BR}R_{press}/(R_{press}+R_A)$$
$$V_B = V_{BR}R_C/(R_C+R_B)$$

for a balanced bridge $V_A = V_B$ or $$R_{press}/(R_{press}+R_A) = R_C/(R_C+R_B)$$

or $$1/(1+R_A/R_{press}) = 1/(1+R_B/R_C)$$

or $$R_{press}/R_A = R_C/R_B$$

if the bridge is not balanced then $V_A \neq V_B$. The bridge resistors are set so that the bridge is balanced when $R_{press}$ is a value chosen to be that which the temperature is fixed. This temperature/resistance relation is $$R = R_O(1+\alpha_1 T + \alpha_2 \Delta T^2)$$

($\alpha_2, \alpha_1$ = temperature coefficients). The resistors $R_A$, $R_B$, $R_C$ are chosen so the $$R_{press}(\text{temperature}) = R_A R_C / R_B$$

The temperature is picked to be higher than the use temperature.

Then if the bridge is not balanced (as with the case where the resistor is at 20° C. and the chosen temperature is 85° C.), at this point the voltage $V_A$ is less than $V_B$ because $$V_A = 1/(1+R_B/R_{press}); R_{press} \downarrow > V_A \downarrow$$

$V_B$ is put to the resistor of the error integrator and $V_A$ is put to the positive side of the opamp. The opamp of the "error integrator" then puts out just enough voltage to the bridge to make $R_{press} = R_A R_B/R_B$ (the correct resistance for the desired temperature). This can be exemplified by thinking of the open loop gain of the opamp $$V_{out} = A(V_B - V_A) \text{ where } A = \infty$$

This means that when $V_A < V_B$ then the $V_{out}$ will be saturated to $\sim V_{supply}$. When $V_A = V_B$ (as when the bridge is balanced) then $V_{out}=0$. The "integrator" function has an actual transfer function of $$V_{out} = 1/RC \int (V_B - V_A) dt$$

This is essentially a slower (more damped) version of the open loop.

The conclusion to this is that the integrator checks to see if the bridge is balanced. If it is, then nothing is done, if it is not, then power is supplied to the bridge until the sensor resistor's temperature is high enough to balance the bridge. This power is given by means of voltage which then becomes the output signal. When the pressure changes, the power loss changes and therefore the amount of power supplied by the integrator is changed to keep the sensor resistor, $R_{press}$, at a constant temperature (and therefore resistance) to balance the bridge.

Figure 9:
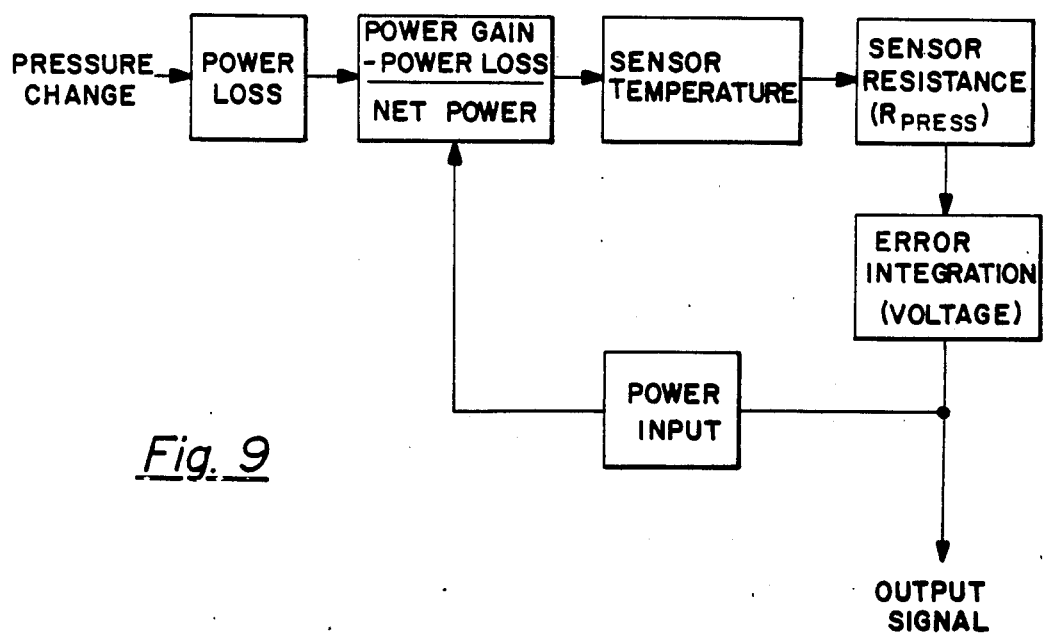
FIG. 9 is a system flow chart for FIG. 8.

FIG. 9 is a functional representation or system flow chart of the above description.

Figure 10:
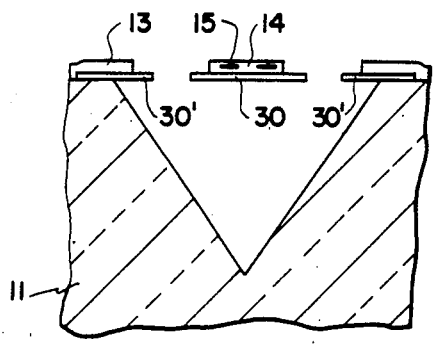
Figure 11:
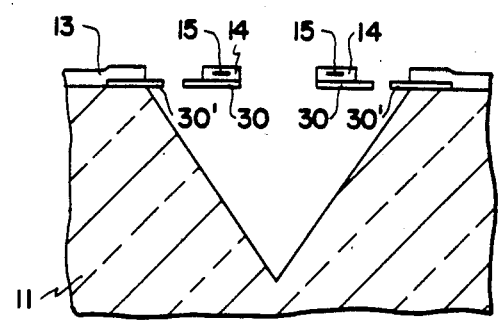
Figure 10A:
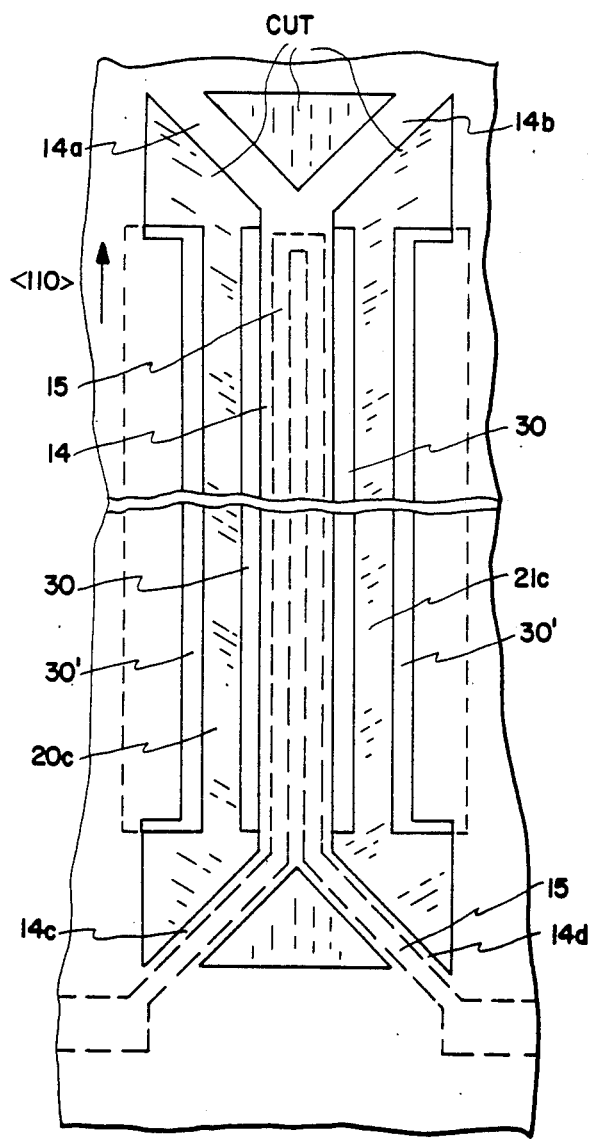
Figure 11A:
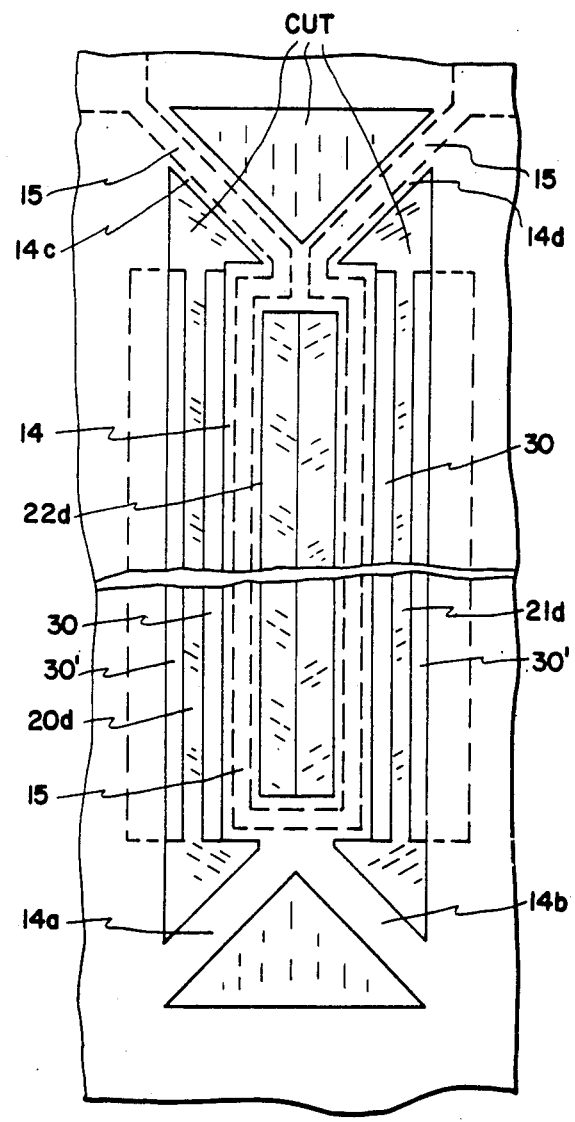

A modified form of the L-shaped etch cuts of FIGS. 1a, 2a and 3a is shown in the additional embodiment of FIGS. 10 and 10a and the embodiment of FIGS. 11 and 11a. The numbering follows that used in FIGS. 3 and 3a as closely as feasible. In this modified form of etch cuts, the end supports or abutments of the nitride bridge are Y-shaped rather than at 90° as in FIGS. 1a, 2a and 3a. That is, the Y-shaped end supports 14a, 14b, 14c and 14d comprise legs at 45° to the 110 direction and narrow enough to undercut from the anisotropic etch.

In FIG. 10a the heater 15 is shown in a U shape on the bridge to double the resistance of the heater on one microstructure as compared with the single run of FIGS. 1a, 2a and 3a. Thus the resistance heater enters at leg 14c, runs the length of the bridge and back and exits at leg 14d. FIG. 11a is a variation of FIG. 10a in that an extra nitride cut 22d is extended down a portion of the center of the bridge 14.

The explanation of the thermal conductivity type microbridge absolute pressure sensor up to this point has been primarily directed to the several embodiments in which an anisotropic etch has been used to create the V-groove beneath the bridging structure. Thus emphasis has been laid on the cavity being oriented with its long axis in the <110> silicon crystal direction in the surface of a (100) silicon wafer. This orientation together with the narrow nitride cuts provided an accurate groove spaced closely to the heated bridge member along the length thereof. Also as has been taught above in connection with the embodiments of FIGS. 2, 2a, 3, 3a, 10, 10a, 11 and 11a there are advantages in providing the thin metal layer 30,30' with the metal edges extending beyond the nitride edges.

We have also discovered that by the use of the metal layer 30,30' arrangement generally shown in FIGS. 3 and 3a to define the edge of the bridge 14 and the edge of the cold sink means, it is possible to use isotropic etching rather than anisotropic to form a groove (not a V-groove) and to more freely orient the direction of the groove. The crystal plane also is now not critical. Referring to FIG. 12, the structure again comprises a heated narrow nitride microbridge 14 suspended over a long cavity 116 etched in the silicon with an isotropic etchant such as a Nitric and HF acid solution. The isotropic etch produces a cavity which has a more bowl shaped cross section since the crystal planes no longer act as etch stops. The bridge element 14 is the thin film silicon nitride bridge within which the NiFe heating resistor 15 is formed. A thin film of metal 30',30 underlies the silicon nitride 13 at the edges of the cavity and the bridge. The spacing 17 between the metal edges 30',30 may be fabricated to be about 2 microns as in earlier described embodiments. The metal 30' extends well onto the silicon substrate 11 and thus is thermally coupled thereto to act as the cold heat sink. In this isotropically etched version of FIG. 12, the bridge can appear more conventional with its abutments directly at the ends of the bridge, because the L-shaped cuts or Y-shaped cuts are not needed.

In FIG. 13 there is shown graphically the measured response to air pressure. This graph plots the log of pressure along the abscissa and an electrical output signal in arbitrary units along the ordinate. The curve shows a useful response over a range from about $10^{-4}$ atmosphere to 10 atmospheres pressure.

The embodiments of the invention in which an exclusive property or right is claimed are defined as follows:

1. A microbridge absolute pressure sensor of the thermal conductivity type for gas or air comprising:
    a silicon microchip having formed thereon a thin film layer of dielectric, said chip having its surface lying in a (100) plane and having a <110> direction;
    two opposing L-shaped cuts through the dielectric, the L-shaped cuts each having a long and a short element with the long elements parallel to the <110> direction of the silicon, said cuts defining a dielectric bridging element therebetween,
    said microbridge having an anisotropically etched groove in the silicon beneath the bridging element and the L-shaped cuts, the cuts exposing the groove through the dielectric layer,
    said dielectric bridging element having two opposing termini, the two opposing termini of the dielectric bridging element being joined to the chip between the long element of one cut and the short element of the other cut at one terminus and between the short element of the one cut and the long element of the other cut at the other terminus, and
    an elongated electrically conductive sensor-heater element formed in and traversing the length of said dielectric bridging element for heating said bridging element, said elongated element entering said bridging element at said one terminus and leaving said bridging element at said other terminus.

2. The sensor according to claim 1 in which the dielectric is silicon nitride.

3. The sensor according to claim 1 in which the groove is a V-shaped groove whose sides terminate on (111) planes.

4. The sensor according to claim 1 in which the groove terminates on the bottom on a heavily doped etch-resistant layer of boron-doped silicon.

5. The sensor according to claim 1 wherein said cuts through the dielectric have a width of about 2 microns.

6. The sensor according to claim 1 wherein the bridging element has a width of about 6 microns and a length of less than 100 microns.

7. The sensor according to claim 1 wherein the groove in the silicon is about 10 microns wide, has a depth of about 7 microns, and a length of less than 100 microns.

8. A microbridge absolute pressure sensor for air or gas comprising:
    a silicon microbridge having formed thereon a thin film layer of silicon nitride, said chip having its surface lying in a (100) plane, said chip having a <110> direction along said plane,
    an elongated V-shaped groove anisotropically etched into said silicon from said surface, said elongated groove having elongated edges oriented in said <110> direction,
    said microchip having an elongated silicon mitride bridging element which has its long edges parallel and proximate to said groove elongated edges, the bridging element having on it a sensor element, said bridging element being attached to said layer at diagonally opposite segments of the long edges,
    an electrically resistance sensor strip formed in said bridging element and extending the length of said bridging element, said strip being adapted to be heated by current flowing therethrough to raise the temperature of said bridging element.

9. The sensor according to claim 8 in which the V-shaped groove has sides terminating on (111) planes.

10. The sensor according to claim 8 in which the bridging element has a width of about 6 microns and a length of less than 100 microns.

11. The sensor according to claim 8 in which the V-shaped groove is about 10 microns wide at the surface, has a depth of about 7 microns, and a length of less than 100 microns.

12. An absolute pressure sensor of the thermal conductivity type for gas or air comprising:
    a silicon microchip having a surface lying in a (100) plane and having a <110> direction, said microchip comprising a cold supporting substrate means for a heated element;
    an anisotropically etched elongated V-groove in said surface parallel to the <110> direction;
    a heated element at the surface of said groove, said element comprising an elongated thin film dielectric strip slightly narrower than said groove, said strip having a major portion of its edges in close proximity to but spaced from the adjacent cold supporting substrate, said strip having ends fastened to said microchip surface, said heated element including means responsive to temperature changes in the film due to thermal conductance changes in the gas.

13. The sensor according to claim 12 in which the elongated thin film dielectric strip is of silicon nitride.

14. The sensor according to claim 12 in which the V-groove has sides terminating on (111) planes.

15. The sensor according to claim 12 in which the dielectric strip has a width of about 6 microns and a length of less than 100 microns.

16. The sensor according to claim 12 in which the V-groove has a width of about 10 microns at the surface, and the dielectric strip has a width of about 6 microns leaving a space of about 2 microns between the strip and the silicon along the length of the strip.

17. The sensor according to claim 12 and further comprising:
    a thin film metal strip comprising a portion of said cold supporting substrate means, said thin film metal strip having an edge positioned parallel with and in close proximity to said heated element, said thin film metal strip mounted to said microchip surface in a position that said metal film edge extends from said surface over a portion of said groove, said metal strip being in good thermal contact with said microchip so that it comprises a portion of said cold supporting substrate means.

18. An absolute pressure sensor of the thermal conductivity type for gas or air comprising:

a silicon microchip having a surface, said microchip comprising a cold supporting substrate means for a heated element;

an etched elongated groove in said surface;

a heated element at the surface of said groove, said element comprising an elongated thin film dielectric strip slightly narrower than said groove, said strip having a major portion of its edges in close proximity to but spaced from the adjacent cold supporting substrate, said strip having ends fastened to said microchip surface, said heated element including means responsive to temperature changes in the film due to thermal conductance changes in the gas; and, said cold supporting substrate means further comprising a thin film metal strip having an edge positioned parallel with and in close proximity to said heated element, said thin film metal strip mounted to said microchip surface in a position that said metal film edge extends from said surface over a portion of said groove, said metal strip being in good thermal contact with said microchip so that it comprises a portion of said cold supporting substrate means.

19. The sensor according to claim 18 in which the elongated thin film dielectric strip is of silicon nitride.

20. The sensor according to claim 18 in which the dielectric strip has a width of about 6 microns and a length of less than 100 microns.

* * * * *